(12) United States Patent
Spencer Jones et al.

(10) Patent No.: US 9,295,483 B2
(45) Date of Patent: Mar. 29, 2016

(54) ROTATABLE PATELLA DRILL GUIDE

(71) Applicant: DEPUY (IRELAND), Cork (IE)

(72) Inventors: Richard Spencer Jones, Shropshire (GB); Abraham P Wright, Winona Lake, IN (US)

(73) Assignee: DEPUY (IRELAND), Cork (IE)

( * ) Notice: Subject to any disclaimer, the term of this patent is extended or adjusted under 35 U.S.C. 154(b) by 0 days.

(21) Appl. No.: 14/736,341

(22) Filed: Jun. 11, 2015

(65) Prior Publication Data

US 2015/0282820 A1 Oct. 8, 2015

Related U.S. Application Data

(63) Continuation of application No. 13/548,598, filed on Jul. 13, 2012, now Pat. No. 9,078,772.

(60) Provisional application No. 61/540,040, filed on Sep. 28, 2011.

(51) Int. Cl.
*A61B 17/17* (2006.01)
*A61F 2/46* (2006.01)
*A61F 2/38* (2006.01)
*A61F 2/30* (2006.01)

(52) U.S. Cl.
CPC ........... *A61B 17/1767* (2013.01); *A61F 2/4684* (2013.01); *A61F 2/3877* (2013.01); *A61F 2002/30225* (2013.01); *A61F 2002/30227* (2013.01); *A61F 2002/30616* (2013.01); *A61F 2002/30878* (2013.01); *A61F 2002/30892* (2013.01)

(58) Field of Classification Search
CPC ............. A61B 17/1767; A61B 17/158; A61B 17/1764; A61B 17/1677
See application file for complete search history.

(56) References Cited

U.S. PATENT DOCUMENTS

| 2,181,746 | A | 11/1939 | Siebrandt |
| 3,835,849 | A | 9/1974 | McGuire |
| D260,927 | S | 9/1981 | Glenn |

(Continued)

FOREIGN PATENT DOCUMENTS

| EP | 791335 A1 | 8/1997 |
| EP | 992222 A2 | 4/2000 |

(Continued)

OTHER PUBLICATIONS

European Search Report, European Patent Application No. 12186675.0-2310, Dated Dec. 12, 2012 (7 Pages).

(Continued)

*Primary Examiner* — Samuel Hanna

(57) ABSTRACT

A patella drill guide includes a base portion rotatably mounted on a bone-gripping component. A trial portion with a contoured articulation surface is above the base portion. The base portion and trial portion have aligned drill guide bores. The base portion and trial portion can be rotated together on the bone-gripping component to optimize the positions of the drill guide bores with respect to the patella surface, thereby optimizing the locations of the mounting pegs of the patella implant component on the patella to optimize the orientation of the patella implant component. The base and the bone-gripping component may be unitary so that the entire assembly rotates on the patella about the central longitudinal axis of the bone-gripping component.

12 Claims, 6 Drawing Sheets

(56) References Cited

U.S. PATENT DOCUMENTS

| | | |
|---|---|---|
| D281,622 S | 12/1985 | Diamond |
| 4,565,192 A | 1/1986 | Shapiro |
| 4,633,862 A | 1/1987 | Petersen |
| 5,002,547 A | 3/1991 | Poggie et al. |
| 5,021,055 A | 6/1991 | Burkinshaw et al. |
| 5,108,401 A | 4/1992 | Insall et al. |
| 5,116,338 A | 5/1992 | Poggie |
| 5,129,907 A | 7/1992 | Heldreth |
| 5,129,908 A | 7/1992 | Petersen |
| 5,147,365 A | 9/1992 | Whitlock et al. |
| 5,222,955 A | 6/1993 | Mikhail |
| 5,250,050 A | 10/1993 | Poggie et al. |
| 5,284,482 A | 2/1994 | Mikhail |
| 5,284,485 A | 2/1994 | Kammerer et al. |
| 5,312,409 A | 5/1994 | McLaughlin |
| 5,382,254 A | 1/1995 | McGarry et al. |
| 5,415,663 A | 5/1995 | Luckman et al. |
| 5,470,328 A | 11/1995 | Furnish et al. |
| 5,484,451 A | 1/1996 | Akopov et al. |
| D367,531 S | 2/1996 | Price et al. |
| 5,520,692 A | 5/1996 | Ferrante |
| 5,536,271 A | 7/1996 | Daly |
| 5,542,947 A | 8/1996 | Treacy |
| D373,635 S | 9/1996 | Price et al. |
| 5,575,793 A | 11/1996 | Carls et al. |
| 5,582,615 A | 12/1996 | Foshee et al. |
| 5,593,450 A | 1/1997 | Scott et al. |
| 5,611,802 A | 3/1997 | Samuelson et al. |
| 5,626,607 A | 5/1997 | Malecki et al. |
| 5,667,512 A | 9/1997 | Johnson |
| 5,716,362 A | 2/1998 | Treacy |
| 5,827,279 A | 10/1998 | Hughett et al. |
| 5,941,884 A | 8/1999 | Corvelli et al. |
| 5,944,723 A | 8/1999 | Colleran |
| 5,968,051 A | 10/1999 | Luckman et al. |
| 6,010,509 A | 1/2000 | Delgado et al. |
| 6,056,754 A | 5/2000 | Haines et al. |
| 6,074,425 A | 6/2000 | Pappas |
| 6,190,391 B1 | 2/2001 | Stubbs |
| 6,205,884 B1 | 3/2001 | Foley et al. |
| D459,474 S | 6/2002 | Bratt et al. |
| 6,419,675 B1 | 7/2002 | Gallo, Sr. |
| D463,550 S | 9/2002 | Sherman |
| 6,855,150 B1 | 2/2005 | Linehan |
| 6,866,667 B2 | 3/2005 | Wood et al. |
| D549,331 S | 8/2007 | Tomatsu et al. |
| 7,344,540 B2 | 3/2008 | Smucker et al. |
| 7,566,335 B1 | 7/2009 | Scott et al. |
| 7,632,279 B2 | 12/2009 | Bastian |
| 7,780,594 B2 | 8/2010 | Hutton |
| 7,806,899 B2 | 10/2010 | Hogg et al. |
| 7,878,989 B2 | 2/2011 | McMinn |
| 7,891,071 B2 | 2/2011 | Collazo |
| D634,011 S | 3/2011 | Phillips et al. |
| D638,541 S | 5/2011 | Claypool |
| 7,972,383 B2 | 7/2011 | Goldstein et al. |
| D642,678 S | 8/2011 | Dockstader et al. |
| D646,389 S | 10/2011 | Claypool et al. |
| 8,216,242 B2 | 7/2012 | Marchyn et al. |
| D667,552 S | 9/2012 | Claypool |
| D667,953 S | 9/2012 | Wright |
| 2002/0115987 A1 | 8/2002 | Hildwein et al. |
| 2003/0163137 A1 | 8/2003 | Smucker et al. |
| 2004/0153066 A1 | 8/2004 | Coon |
| 2004/0162561 A1 | 8/2004 | Marchyn et al. |
| 2005/0240196 A1 | 10/2005 | Davis et al. |
| 2006/0142777 A1 | 6/2006 | Bastian |
| 2007/0118141 A1 | 5/2007 | Marchln et al. |
| 2007/0233142 A1 | 10/2007 | Oliver |
| 2007/0260227 A1 | 11/2007 | Phan |
| 2008/0097450 A1 | 4/2008 | Brown et al. |
| 2008/0114366 A1 | 5/2008 | Smucker et al. |
| 2008/0177394 A1 | 7/2008 | Chauhan |
| 2008/0228190 A1 | 9/2008 | Sherry et al. |
| 2008/0306484 A1 | 12/2008 | Coon |
| 2009/0264737 A1 | 10/2009 | Haechler et al. |
| 2009/0326661 A1 | 12/2009 | Wright et al. |
| 2010/0030223 A1 | 2/2010 | Kellar |
| 2010/0152742 A1 | 6/2010 | Nevelos et al. |
| 2010/0168753 A1 | 7/2010 | Edwards et al. |
| 2011/0066193 A1* | 3/2011 | Lang et al. ............ 606/86 R |
| 2012/0078261 A1 | 3/2012 | Kecman et al. |
| 2013/0023883 A1 | 1/2013 | Wright |
| 2013/0023890 A1 | 1/2013 | Kecman |
| 2013/0030443 A1 | 1/2013 | Wright |
| 2013/0030539 A1 | 1/2013 | Wright |
| 2013/0035693 A1 | 2/2013 | Wright |
| 2013/0079787 A1 | 3/2013 | Spencer Jones |
| 2013/0079789 A1 | 3/2013 | Randle |
| 2013/0211410 A1 | 8/2013 | Landes |

FOREIGN PATENT DOCUMENTS

| | | |
|---|---|---|
| EP | 1723916 A1 | 11/2006 |
| EP | 1967143 A2 | 9/2008 |
| EP | 2574314 A1 | 4/2013 |
| FR | 2737848 A1 | 2/1997 |
| WO | WO 9945856 A1 | 9/1999 |
| WO | WO 2005110249 A1 | 11/2005 |
| WO | WO 2008112996 A1 | 9/2008 |

OTHER PUBLICATIONS

European Search Report, European Patent Application No. 12186700.6-2310, Dec. 13, 2012 (8 Pages).

European Search Report, European Patent Application No. 12186728.7-2310, Dated Dec. 14, 2012 (8 Pages).

European Search Report, European Patent Application No. 11175824.9-2310, Dated Dec. 16, 2011 (7 Pages).

European Search Report, European Patent Application No. 12191753.8-2310, Dated Mar. 1, 2013 (7 pages).

Australian Search Report for Patent Application No. 2012227341 Dated Jun. 13, 2014, (3 Pages).

DePuy International Ltd., PFC Sigma Rotating Platform Knee System with MBT Tray, Surgical Technique, 2003 (43 pages) Cat. No. 9068-96-000.

DePuy Orthopaedics, Inc., LCS High Performance Instruments, Surgical Technique Guide, 2008, (44 pages) Pub. No. 0612-85-506.

DePuy Orthopaedics, Inc., Sigma High Performance Instruments, Design Rationale, 2009 (12 pages), Pub. No. 0612-54-506 (Rev. 2).

DePuy Orthopaedics, Inc., Sigma High Performance Instruments, Classic Surgical Technique, 2010 (52 pages), Pub. No. 0612-89-510.

* cited by examiner

ROTATABLE PATELLA DRILL GUIDE

CROSS-REFERENCE TO RELATED APPLICATION

This application claims priority to U.S. Prov. App. No. 61/540,040 entitled "Rotatable Patella Drill Guide," filed Sep. 28, 2011. The present application is also a continuation of U.S. Publication No. 20130079787A1 (U.S. patent application Ser. No. 13/548,598) entitled "Rotatable Patella Drill Guide" filed on Jul. 13, 2012, both of which are incorporated by reference herein in their entireties.

TECHNICAL FIELD

The present disclosure relates generally to orthopaedic surgical instruments and more particularly to patella drill guides.

BACKGROUND

During the lifetime of a patient, it may be necessary to perform a joint replacement procedure on the patient as a result of, for example, disease or trauma. The joint replacement procedure may involve the use of a prosthesis which is implanted into one or more of the patient's bones. In the case of a patella replacement procedure, an orthopaedic prosthesis is implanted into the patient's patella. Specifically, a prosthetic patella implant component is secured to the patient's natural patella such that its posterior surface articulates with a femoral component during extension and flexion of the knee.

To facilitate the replacement of the articulating surface of the natural patella with the prosthetic patella, orthopaedic surgeons use a variety of orthopaedic surgical instruments such as, for example, saws, drills, mills or reamers to resect the posterior surface of the patella and then to prepare the resected surface for fixation of the prosthetic patella.

Common fixation elements for prosthetic patellae include one or more pegs extending out from the bone-facing (anterior) surface to be received in complementary recesses or holes drilled or reamed into the patella.

In some prosthetic patella implants, the articulating surface is dome-shaped, as in U.S. Pat. No. 5,593,450. In other types of prosthetic patella implants, the articulating surface has an asymmetric shape to be received and track within the patellar groove in the prosthetic femoral implant component. An example of such an asymmetrically-shaped prosthetic patella is disclosed in U.S. Pat. No. 6,074,425. With such asymmetric patella implants, rotational alignment of the implant impacts the way in which the patella implant tracks in the trochlear groove of the femoral implant. Such asymmetric patella implants typically include a plurality of pegs extending out from the anterior surface to be received in the complementary holes drilled in the patella surface. However, the surgeon typically cannot fully evaluate patellar tracking until trial patellar and femoral components are in place, which generally requires that the complementary holes be drilled before the trial is placed on the resected patella. If the surgeon determines that the patella trial does not track correctly, there is little opportunity to make adjustments since the mounting holes have already been drilled into the resected patella surface.

SUMMARY

The present invention provides a patella drill guide that allows the surgeon to evaluate patella tracking before drilling mounting holes into the resected surface of the patella.

In illustrative embodiments, the present invention provides such a patella drill guide for use in preparing a resected patellar bone surface to receive a prosthetic patellar implant component. The patella drill guide comprises a bone-gripping component, a base portion and a patella trial portion. The bone-gripping component is for gripping a portion of the resected patellar bone surface. The base portion has a flat patella bone-facing surface and a portion of the bone-gripping component extends outwardly from the flat patella bone-facing surface of the base. The patella trial portion has a contoured articulation surface spaced above the flat patella bone-facing surface of the base portion. The base portion has a plurality of drill guide bores extending through the base portion to the flat patella bone-facing surface of the base portion.

In a particular embodiment, the base is rotatably mounted on the bone-gripping component. In such an embodiment, the positions of the drill guide bores with respect to the resected patellar surface change as the base portion is rotated on the bone-gripping component.

Such a patella drill guide can be temporarily mounted on the resected posterior surface of the patella and used to evaluate the size and set the orientation of the patella trial portion prior to drilling holes in the patella; once the surgeon is satisfied with the orientation of the patella trial portion, the surgeon may use the patella drill guide to drill properly oriented and positioned holes to receive and properly orient the patella implant component.

In a more particular embodiment, the bone-gripping component comprises a pedestal and a plurality of spikes extending outwardly from a pedestal. In this embodiment, the base is rotatably mounted on the pedestal.

In another more particular embodiment, the patella trial portion has a plurality of bores aligned with the drill guide bores of the base. The alignment of the drill guide bores and bores of the patella trial portion does not change as the base portion is rotated on the bone-gripping component. In such a device with aligned bores in the patella trial portion, the portion of each bore through the patella trial portion may have a larger diameter than the aligned portion of such bore through the base portion.

In another more particular embodiment, the base portion and the patella trial portion are integral.

In another more particular embodiment, the base portion and the patella trial portion comprise independent components connected to define an assembly. In this embodiment, the base portion may have an upper or second surface spaced from and parallel to the flat patella bone-facing surface. In such an embodiment, the base portion may have an edge that extends between the upper surface and the patella bone-facing surface. The edge may include a plurality of spaced recesses and the upper surface may include indicia adjacent to the spaced recesses. In such an embodiment, the patella trial portion may have a flat surface spaced from the contoured articulation surface and the flat surface of the patella trial portion may be fixed to the second flat surface of the base. In such an embodiment, the base portion may have a constant thickness or alternatively may have an thicker portion adjacent to the drill guide bores and thinner portions adjacent to the spaced recesses.

In another more particular embodiment, the base portion includes a first end portion and a second end portion connected by an arm. In this embodiment, the first end portion of the base portion is rotatably mounted on the bone-gripping component, the patella trial portion is part of the first end portion of the base portion and the second end portion of the patella drill guide includes a second bone-gripping component, a second base portion having a flat patella bone-facing surface, and a second patella trial portion having a contoured articulating surface. In this embodiment, the second base portion is rotatably mounted on the second bone-gripping component with a portion of the second bone-gripping component extending outwardly from the flat patella bone-facing surface, the second patella trial portion has a contoured articulation surface spaced above the flat patella bone-facing surface of the second base portion and the second base portion and the second patella trial portion have a plurality of aligned drill guide bores extending from the contoured articulation surface of the second patella trial portion, through the second patella trial portion and through the second base portion to the flat patella bone-facing surface of the second base portion. The alignment of the drill guide bores of the second base portion and second patella trial portion does not change as the second base portion is rotated on the second bone-gripping component and the positions of the aligned drill guide bores of the second end portion with respect to the resected patellar surface changes as the second base portion is rotated on the second bone-gripping component.

In this embodiment, the second bone-gripping component may comprise a pedestal and a plurality of spikes extending outwardly from the pedestal.

In this embodiment, a portion of each bore through the second patella trial portion may have a larger diameter than the aligned portion of such bore through the second base portion.

In this embodiment, the second base portion and the second patella trial portion may be integral or may comprise independent components connected to define an assembly.

In this embodiment, the contoured articulation surface of the second patella trial portion may be asymmetric.

In this embodiment, the second end portion of the patella drill guide may have a thickness extending from the contoured articulation surface of the second patella trial portion to an exposed surface of the second base portion, the second patella trial portion may have edges, including opposite edges. The thickness of the second end portion of the patella drill guide may vary from one edge of the second patella trial portion to the opposite edge and in at least one cross-sectional view, and the maximum thickness of the second end portion of the patella drill guide may be at a position between the opposite edges of the second patella trial portion at a distance from one edge of more than half the distance between the opposite edges.

In this embodiment, the first and second patella trial portions may be of different size, and the distance between opposite edges of the first patella trial portion may be different from the distance between the opposite edges of the second patella trial portion.

In another more particular embodiment, the patella drill guide further comprises a handle and a clamping mechanism connected to the handle. In this embodiment, the handle is connected to the base portion of the patella drill guide. In this embodiment, the clamping mechanism may comprise a cantilever spring member extending from the handle to an end spaced from and aligned with the base portion and a bone-gripping member on the end of the cantilever spring member facing and spaced from the bone-gripping component on the base portion. In this embodiment, the clamping mechanism may further comprise a deflector connected to the handle and operable to selectively deflect the bone-gripping member on the cantilever spring member away from the bone-gripping component on the base portion.

BRIEF DESCRIPTION OF THE DRAWINGS

The detailed description particularly refers to the following figures, in which.

DETAILED DESCRIPTION OF THE DRAWINGS

Figure 1:
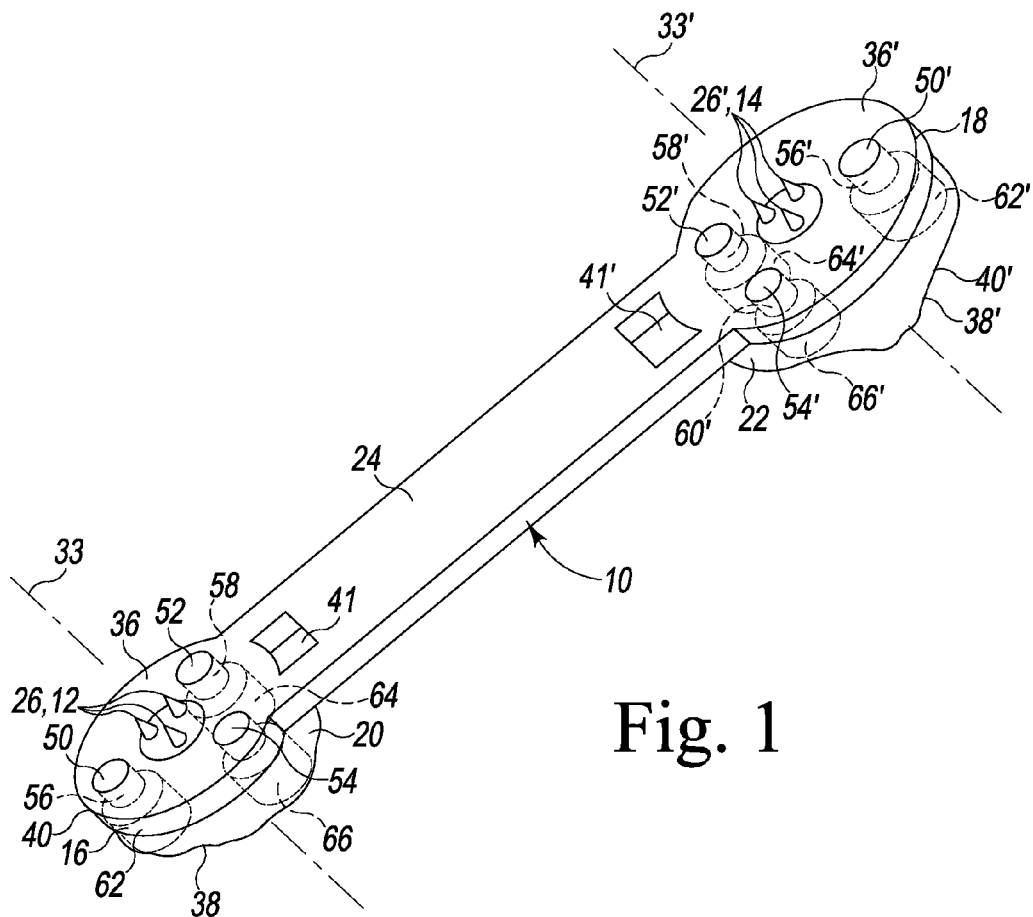
FIG. 1 is a perspective view of one embodiment of a patella drill guide incorporating the principles of the present invention.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring to FIG. 1, a first embodiment of a patella drill guide 10 is illustrated. The illustrated patella drill guide 10 comprises a first bone-gripping component 12, a second bone-gripping component 14, a first base portion 16, a second base portion 18, a first patella trial portion 20, a second patella trial portion 22 and an arm 24 connecting the two base portions 16, 18. In the first embodiment, the first and second bone-gripping components 12, 14 are rotatably retained on the first and second base portions 16, 18.

Together, the first bone-gripping component 12, first base portion 16 and first patella trial portion 20 comprise a first end portion of the illustrated patella drill guide 10, and the second bone-gripping component 14, second base portion 18 and second patella trial portion 22 comprise a second end portion. It should be understood that the first and second end portions in the illustrated embodiment differ only in size. Only the details of first end portion are described below. It should be understood that the following detailed description of the first end portion applies to the second end portion as well unless expressly distinguished. In the drawings, parts of the second end portion that correspond with parts of the first end portion are identified with the same reference number as that used for the first end portion, followed by the prime symbol "'".

Figure 12:
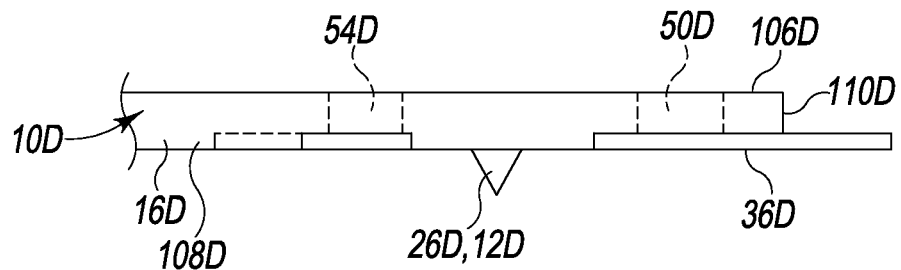
FIG. 12 is a side elevation of another alternative base portion of a patella drill guide that may be used with the patella trial component of FIG. 7.
Figure 13:
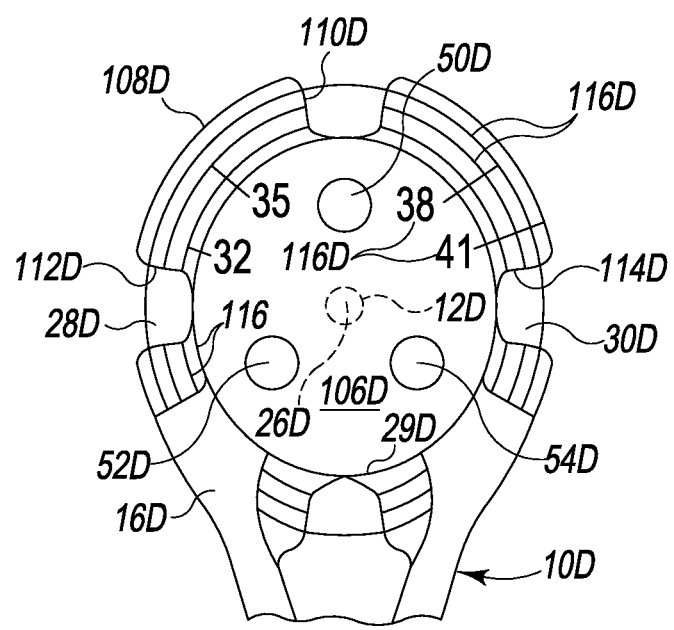
FIG. 13 is a top plan view of the base portion of FIG. 12.

In the first illustrated embodiment, the first and second bone-gripping components 12, 14 comprise a plurality of pointed conical spikes 26. The spikes are sized and shaped to be pushed into the resected posterior surface of a patella, such as surface 28 of patella 30 in FIGS. 3-4. Although three conical spikes 26 are shown in the accompanying drawings, it should be understood that fewer or more spikes can be used; example, a single spike 26D could be used, as shown in the embodiment of FIGS. 12-13.

Figure 3:
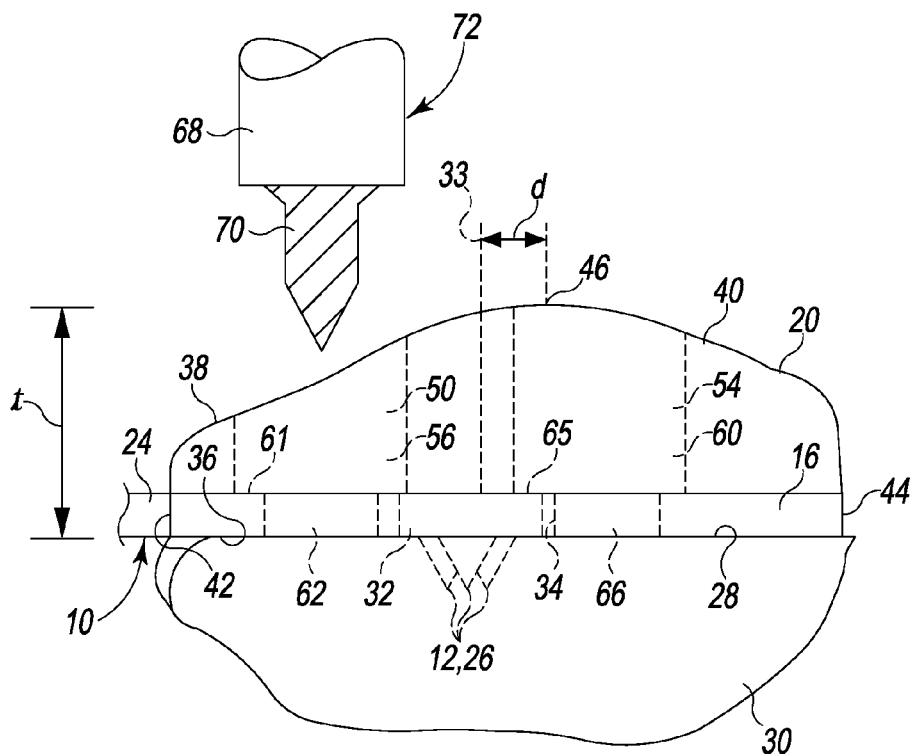
FIG. 3 is an enlarged side view of one end portion of the patella drill guide of FIGS. 1-2, illustrating the end portion secured to a resected patella and with an example of a suitable countersink, depth-controlling drill bit.

As shown in phantom in FIG. 3, the spikes 26 of the first illustrated bone-gripping component 12 are fixed to a pedestal 32 and extend outwardly from the pedestal 32. The pedestal 32 may have a generally cylindrical outer surface and include mounting features so that the first base portion 16 may be rotatably mounted on the pedestal 32 of the first bone-gripping component 12. The first base portion 16 may include a cylindrical recess 34 (see FIGS. 3-4) to receive the pedestal 32. The pedestal 32 and first base portion 16 may include complementary structures to secure the pedestal 32 and base portion 16 together while allowing for relative rotation about the central longitudinal axis 33 of the pedestal 32; such complementary structures could include, for example, a groove and a set of flexible projections to allow the pedestal 32 to be snap-fit into the recess 34 of the base portion 16 while allowing for full rotation about axis 33.

Other options are available for rotatably connecting the pedestal 32 and the base portion 16. For example, a screw and a roller bearing could be used. Alternatively, the pedestal could be shaped to have a larger diameter than the portion carrying the spikes 26, and a cover with a hole having a diameter greater than the diameter of the portion carrying the spikes 26 and less than the diameter of the portion of the pedestal retained within the recess in the base portion; thus, the pedestal 32 can be secured to the base portion 16 while allowing full relative rotation between these components.

It may be desirable to provide for locking the pedestal 32 and base portion 16 in a plurality of relative rotational positions. For example, the outer surface of the pedestal 32 could comprise a ratcheted surface, and a pawl could be mounted within the base portion 16 so that the pedestal and base releasable lock into a number of positions. Other locking mechanisms could be employed as well.

If a single spike is used, it may not be necessary for the base to be rotatably mounted on the base. Instead, the base and spike could be rotated about the spike on the patella. Such an embodiment is illustrated in FIGS. 12-13.

Figure 4:
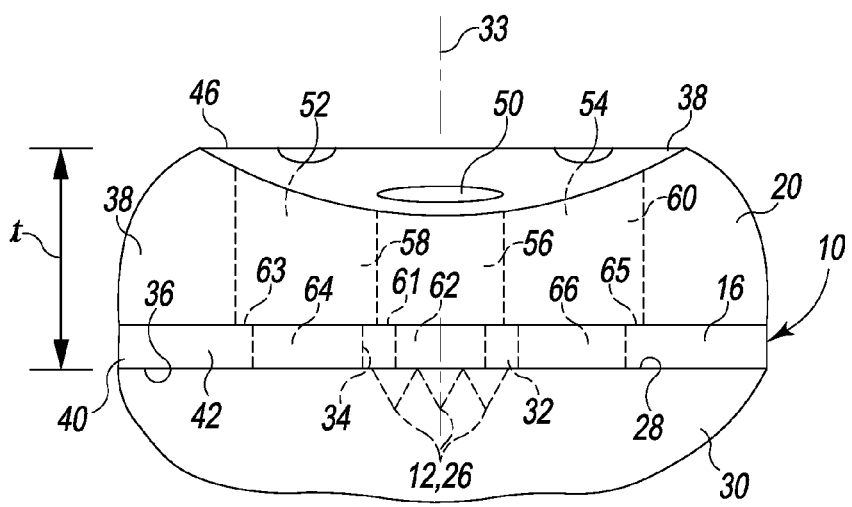
FIG. 4 is an enlarged side view of the patella drill guide of FIG. 3 with the base and patella trial of the drill guide turned ninety degrees from the position shown in FIG. 3, shown secured to a resected patella but without the countersink, depth-controlling drill bit.

The base portion 16 includes a flat, planar patella bone-facing surface 36. As shown in FIGS. 3-4, this surface 36 is designed to be pressed flat against the posterior resected surface 28 of a patella 30. The recess 34 is open through the surface 36 so that the spikes 26 extend outwardly beyond the patella bone-facing surface 36.

In the illustrated embodiment, the patella trial portion 20 has a contoured articulation surface 38 spaced above the flat, planar patella bone-facing surface 36 of the base portion 16. The contoured articulation surface 38 may be an anatomic one, such as is disclosed in U.S. Pat. No. 6,074,425, which is incorporated by reference herein in its entirety. The contoured articulation surface may be shaped as disclosed in U.S. Pat. No. 7,972,383 or U.S. Pat. Publ. No. 2009-0326661 A1, which are incorporated by reference herein in their entireties. The contoured articulation surface may also comprise a sombrero-shaped or semi-sombrero-shaped surface. In general, the articulation surface 38 is contoured to be shaped like the shape of the corresponding size of patella implant component.

In the illustrated embodiment, the distance between the contoured articulation surface 38 and the flat, planar patella bone-facing surface 36 defines the overall thickness of the end portion 40 of the patella drill guide 10, and generally corresponds with the thickness of the corresponding patella implant component. As shown in FIG. 3, the thickness of the end portion 40 varies from one edge 42 of the end portion 40 to an opposite edge 44 of the end portion 40 when viewed in a coronal plane. The maximum thickness of the end portion 40 is at the peak 46 of the articulation surface 38, shown as thickness "t" in FIGS. 3 and 4. The peak 46 is off-center in the illustrated embodiment, being located at a position between the opposite edges 42, 44 at a distance more than one half the distance between the opposite edges 42, 44; this offset is shown in FIG. 3 as distance "d" from the central axis 33 of the pedestal 32, the central axis 33 being one-half the distance between the edges 42, 44.

The base portion 16 and the patella trial portion 20 of the first illustrated embodiment have a plurality of aligned drill guide bores 50, 52, 54 extending from the articulation surface 38 of the patella trial portion 20, through the body of the patella trial portion 20 and through the base portion 16 to the flat patella bone-facing surface 36 of the base portion 16. As shown in FIG. 4, each drill guide bore 50, 52, 54 comprises two portions: the portion 56, 58, 60 through the patella trial portion 20 and the aligned portion 62, 64, 66 through the base portion 16. The portions 56, 58, 60 through the patella trial portion 20 have larger diameters than the portions 62, 64, 66 through the base portion 16, and define annular shoulders, shown in FIGS. 3 and 4 at 61, 63 and 65. The diameters of these portions 56, 58, 60, 62, 64, 66 correspond with the diameters of a collar portion 68 and fluted portion 70 of the countersink drill bit 72, shown in FIG. 3; the diameters of the portions 62, 64, 66 through the base portion 16 correspond with the diameters of the mounting pegs on the patella implant component. In use, the annular shoulders 61, 63, 65 limit movement on the drill bit 72 into the patella 30 by serving as a stop for the collar portion 68 of the drill bit 72; the thickness of the base portion 16 and the length of the fluted portion 70 of the drill bit thereby control the depth of the holes drilled into the patella. This depth generally corresponds with the lengths of the mounting pegs on the patella implant component.

Figure 2:
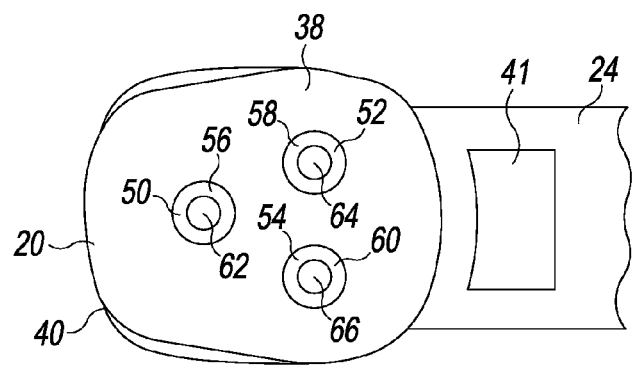
FIG. 2 is a top plan view of one end portion of the patella drill guide of FIG. 1.

As can be seen in FIGS. 1 and 2, the aligned bores 50, 52, 54 in the illustrated embodiment are spaced in a triangular pattern on the end portion 40. The number of bores and spacing between the bores 50, 52, 54 correspond with the number and spacing of the mounting pegs on the patella implant component. It should be understood that the number and spacing of the bores may be adjusted from the illustrated embodiment, depending on the number and spacing of the mounting pegs on the patella implant component.

In the first illustrated embodiment, the base portion 16 and patella trial portion 20 are discrete, independent components that are connected to define an assembly. Although not illustrated, it should be understood that any suitable connection mechanism may be used to assemble these components 16, 20, such as complementary projections and recesses for a snap fit arrangement. It may be desirable to allow the surgeon to change the patella trial portions 20 intraoperatively so that different sizes or shapes of articulation surfaces may be trialed on the same base portion 16. It should also be understood that the base portion 16 and patella trial portion 20 may instead comprise a single, integral component.

Trialing of different sizes of patella implant components can be accomplished with the illustrated embodiment. As indicated above, the illustrated patella drill guide 10 includes a second end portion 40' at the opposite end of the arm 24. The second end portion 40' in the illustrated embodiment is substantially the same as the first end portion 40, differing only in size. The above description of the first end portion 40 thus applies to the second end portion 40' as well. With the illustrated embodiment, the surgeon may trial two different sizes of components before drilling the holes for the mounting pegs. Although the illustrated embodiment has two similar end portions 40, 40', it should be understood that a patella drill guide utilizing the principles of the present invention may include only a single end portion. In addition, a surgical kit may include multiple patella drill guides, either single or double-ended, to provide the surgeon with multiple sizes of patella trial portions to use as trials.

In the embodiment illustrated in FIG. 1, the arm 24 connecting the two end portions 40, 40' may optionally include cutouts 41, 41' defining windows through which the surgeon may see the edge of the patella when the drill guide 10 is mounted on the patella.

Figure 5:
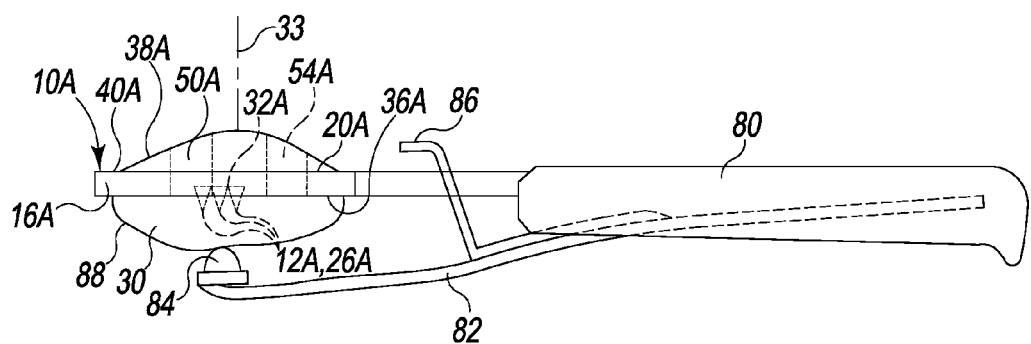
FIG. 5 is a side elevation view of an alternative embodiment of the patella drill guide, shown clamping a resected patella.
Figure 6:
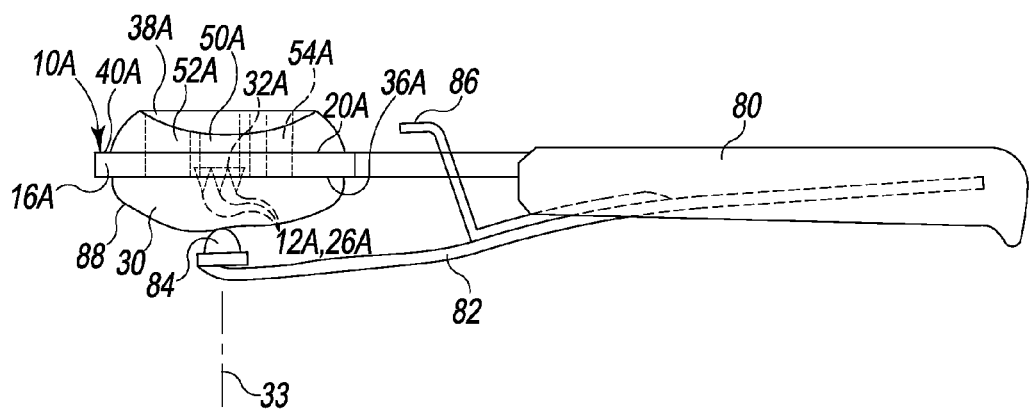
FIG. 6 is a side elevation view of the embodiment of the patella drill guide of FIG. 5, shown with the patella drill guide pivoted 90 degrees with respect to the patella.
Figure 7:
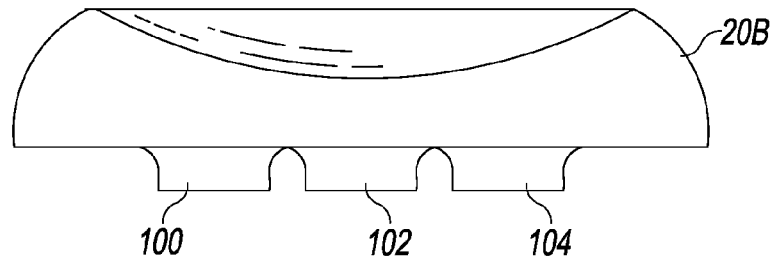
FIG. 7 is a side elevation view of an embodiment of a patella trial component.

The patella drill guide of the present invention may also include other features. For example, a clamping mechanism may be included for clamping the patella drill guide against the posterior surface of the patella. An example of such a clamping mechanism is illustrated in the embodiment of FIGS. 5-6. Many of the features of this embodiment are similar to the features of the first embodiment described above; for such similar features, the same reference numbers have been used in FIGS. 5-6, followed by the letter "A". It should be assumed that the above description applies as well to features bearing the same reference numerals in FIGS. 5-6 as in FIGS. 1-4.

In the patella drill guide 10A of FIGS. 5-6, there is a single end portion 40A having features like those described above. Instead of being connected to a second end portion, the end portion 40A of FIGS. 5-6 is connected to a handle 80. The handle 80 also houses one end of a cantilever spring element 82 that extends from the handle 80 to a second end aligned beneath the base portion 16A. The second end of the cantilever spring element 82 carries a bone-gripping member 84 that is aligned along the central axis 33 of the pedestal 32. The bone-gripping member 84 can be deflected away from the base portion 16A by depressing a deflector 86 that operates against a portion of the cantilever spring element 82 between the two ends of the spring element 82. In use, the bone-gripping member 84 acts against the anterior surface 88 of the patella 30 so that the patella is effectively held between the bone-gripping member 84 and the patella bone-facing surface 36A of the base portion 16A. As can be seen from FIGS. 5-6, the clamp defined by the bone-gripping member 84, spring element 82, handle 80 and end portion 40A allow for the spikes 26A of the end portion 40A to be set into the resected patella surface and allow for full rotation of the base portion 16A, patella trial portion 20A and bone-gripping member 84 about the pedestal 32A so that the surgeon may have a firmer hold of the patella as the trialing and drilling processes are performed.

It should be understood that the specific clamping mechanism described above and illustrated in FIGS. 5-6 is one example of a suitable clamping mechanism. Other clamping mechanisms may be used with the rotatable drill guide and are within the scope of the invention unless expressly limited to a particular clamping mechanism.

Other alternative embodiments are illustrated in FIGS. 7-9, FIGS. 10-11 and FIGS. 12-13. Many of the features of these embodiments are similar to the features of the embodiments described above; for such similar features, the same reference numbers have been used in FIGS. 7-9, followed by the letter "B", in FIGS. 10-11, followed by the letter "C" and in FIGS. 12-13, followed by the letter "D". It should be assumed that the above description applies as well to features bearing the same reference numerals in FIGS. 7-13 as in FIGS. 1-6 unless specific differences are called out.

In these embodiments, the base portion 16B, 16C, 16D and the patella trial portion 20B are discrete independent components that are assembled for use. However, in these embodiments, the patella trial portion 20B does not have any guide bores. Instead, the patella trial portion 20B has a plurality of pegs 100, 102, 104 that are sized and positioned to be received within the drill guide bores 50B, 52B, 54B, 50C, 52C, 54C, 50D, 52D, 54D that extend from the upper surface 106, 106C, 106D to the patella bone-facing surface 36B, 36C, 36D of the base portion 16B, 16C, 16D. The base portion 16B, 16C, 16D has an edge 108, 108C, 108D that extends between the upper surface 106, 106C, 106D and the patella bone-facing surface 38B, 38C, 38D and around part of the circumference of the base portion 16B, 16C, 16D. For these embodiments, the patella trial portion 20B has a reduced thickness, to account for the thickness of the base portion 16B, 16C, 16D when trialing the assembly on the patella.

FIGS. 9-13 illustrate some optional additional features that may be used with the base portion 16B, 16C, 16D of FIGS. 8-13. In these embodiments, the edge 108, 108C, 108D includes a plurality of spaced cut-outs or recesses 110, 112, 114, 110C, 112C, 114C, 110D, 112D, 114D through which the resected posterior surface 28B, 28C, 28D of the patella 30B, 30C, 30D may be viewed. The upper surface 106, 106C, 106D of the base portion 16B, 16C, 16D includes sizing indicia 116, 116C, 116D so that the surgeon can view the resected patella surface 28B, 28C, 28D juxtaposed with the sizing indicia 116, 116C, 116D to determine the optimum size of patella implant component to be implanted. These embodiments are particularly beneficial if multiple sizes of patella implant components have commonly sized and positioned mounting pegs, so that the same drill guide 10B, 10C, 10D can be used for multiple sizes of patella implant components.

Figure 8:
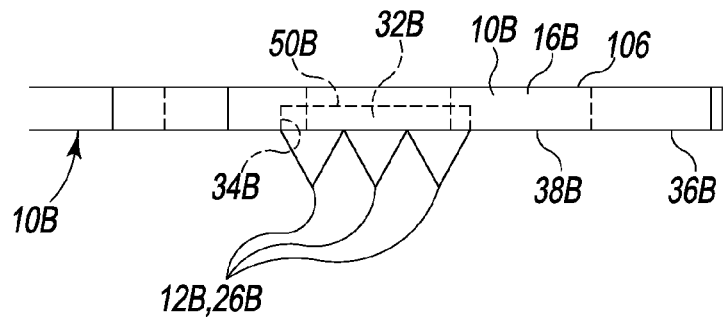
FIG. 8 is a side elevation view of an alternative base portion of a patella drill guide for use with the patella trial component of FIG. 7.
Figure 9:
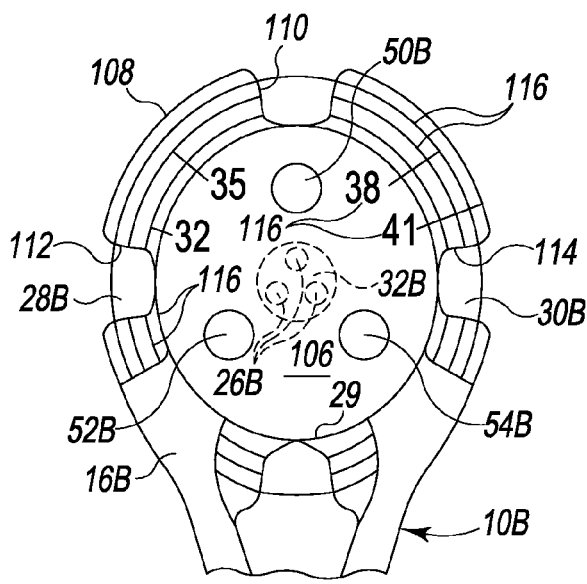
FIG. 9 is a top plan view of an alternative base portion of a patella drill guide that may be used with the patella trial component of FIG. 7.

In the embodiment of FIGS. 8-9, the base portion 16B has a constant thickness between the upper surface 106 and the patella bone-facing surface 36B; the thickness corresponds with the thickness of the pegs 100, 102, 104 of the trial portion 20B. In the alternative embodiments of FIGS. 10-13, the thickness of the base portion 16C, 16D varies: near the cut-outs or recesses 110C, 112C, 114C, 110D, 112D, 114D the thickness of the base portion 16C, 16D is less than the thickness near the drill guide bores 50C, 52C, 54C, 50D, 52D, 54D; for example, the thickness of the base portion 16C, 16D near the cut-outs or recesses 110C, 112C, 114C, 110D, 112D, 114D may be about 2 mm, while the thickness of the base portion 16C, 16D near the drill guide bores 50C, 52C, 54C, 50D, 52D, 54D may be about 6 mm. The varying thickness of the base portion may be advantageous in that the relatively thin areas around the cut-outs or recesses 110C, 112C, 114C, 110D, 112D, 114D, make the size markings 116C, 116D more proximate to the patella bone surface 28C, 28D and therefore more readable. In addition, the thicker center section around the drill guide bores 50C, 52C, 54C, 50D, 52D, 54D may be useful in reducing the number of drill bits included in the instrument set. Typically, an instrument set would include a drill bit with a depth stop for drilling holes at the appropriate depth to receive pegs of other components, such as the femoral implant component. The thicker center section of the base portion 16C, 16D would allow this same drill bit, with the same depth stop, to be used to drill the holes for the patella implant component at the appropriate depth for the patella implant component.

Figure 10:
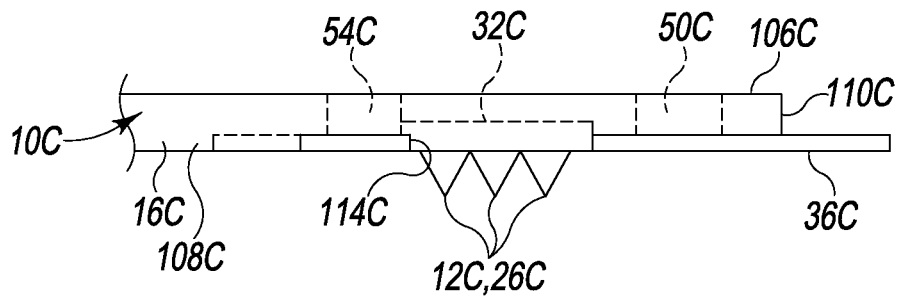
FIG. 10 is a side elevation of another alternative base portion of a patella drill guide for use with the patella trial component of FIG. 7.
Figure 11:
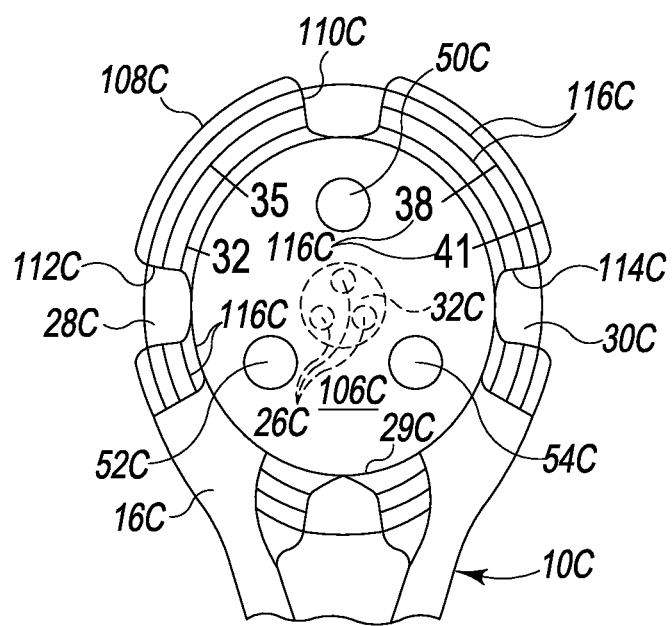
FIG. 11 is a top plan view of the base portion of the patella drill guide of FIG. 10

The embodiment of FIGS. 12-13 differs from that of FIGS. 10-11 in that the bone-gripping component 12D in the embodiment of FIGS. 12-13 comprises a single spike 26D fixed to the base portion 16D. With this embodiment, the entire assembly, including the base portion 16D, trial portion 20D and spike 26D, rotate as a unit about a longitudinal axis through the spike 26D when the spike is pressed into the resected surface 28D of the patella 30D. Such a fixed spike 26D could also be used in place of the plurality of spikes 26, 26A, 26B, 26C mounted on a pedestal 32, 32A, 32B, 32C, as in the embodiments of FIGS. 1-11.

Although there are advantages to using the trialing and guide system illustrated in FIGS. 7-13, it should be understood that variations may be made. For example, the discrete patella trial portion 20B could include guide bores that will align with the guide bores 50B, 52B, 54B when the trial portion 20B and base portion 16B, 16C are assembled. In such an embodiment, a mounting mechanism other than the pegs 100, 102, 104 would be employed. In addition, although advantageous, the base portion 16B, 16C need not include the cut-outs/recesses 110, 112, 114 or sizing indicia 116.

All of the illustrated embodiments may be made of standard polymeric or metallic materials used in the field of surgical instruments, and may comprise assemblies of different such materials. Conventional manufacturing processes may be used. The invention is not limited to any particular material or manufacturing process unless expressly called for in the claims.

In use, the surgeon would first prepare the patella by resecting the posterior surface of the patella to create a flat, planar surface, such as surface 28 of patella 30. For the embodiments of FIGS. 1-6, the surgeon would then estimate the size of patella implant component that would be needed by the particular patient and select an appropriately sized patella drill guide, such as drill guide 10, and then select the appropriately sized end portion, such as first end portion 40. The surgeon would then push the spikes 26 of the first bone-gripping component 12 into the resected bone surface 28 until the patella bone-facing surface 36 of the base portion 16 is flat against the resected bone surface 28. With the end portion 40 thus fixed to the patella 30, the patella may be positioned so that the articulation surface 38 of the patella trial portion 20 engages an articulation surface of the femoral trial component (not shown). The surgeon can then take the patient's knee through a range of flexion and extension, and evaluate the interaction of the patellar trial articulation surface 38 and the articulation surface of the femoral trial component. As the patient's knee is taken through the range of motion, the surgeon may adjust the orientation of the patella trial portion 20 by turning the base portion 16, 16A, 16B, 16C and attached patella trial portion 20, 20A, 20B on the pedestal 32, 32A, 32B, 32C until the surgeon is satisfied that the orientation of the articulation surface 38, 38A, 38B is optimum. In the case of the embodiment of FIGS. 12-13, the base portion 16D and attached patella trial portion 20D are turned about the axis through the spike 26D until the surgeon is satisfied that the orientation of the articulation surface 38B is optimum. Since the orientation of the aligned bores 50, 52, 54, 50A, 52A, 54A, 50B, 52B, 54B, 50C, 52C, 54C, 50D, 52D, 54D with respect to the patella changes as the base portion 16, 16A, 16B, 16C, 16D and attached patella trial portion 20, 20A, 20B are turned, the bores 50, 52, 54, 50A, 52A, 54A, 50B, 52B, 54B, 50C, 52C, 54C, 50D, 52D, 54D should then be in the optimum orientation and position. The surgeon may then drill through the optimally-located bores 50, 52, 54, 50A, 52A, 54A, 50B, 52B, 54B, 50C, 52C, 54C, 50D, 52D, 54S to create mounting holes in the patella. The depth of each hole may be set if the drill bit has a collar and bores include shoulders, such as collars 68 and shoulders 63 shown in FIG. 3. The patella drill guide 10, 10A, 10B, 10C, 10D may then be removed from the prepared patella and the patella implant component may be implanted, with its mounting pegs received in the drilled holes and its orientation optimized for proper tracking with respect to the femoral implant component.

For the embodiments of FIGS. 7-13, a surgical kit using the features of this embodiment could include multiple sizes of patella trial portions 20B corresponding with each size of implant component. The surgeon would mount the base portion 16B, 16C, 16D on the resected surface 28B, 28C, 28D of the patella by pressing the spikes 26B, 26C or spike 26D into the patella surface 28B, 28C, 28D and observing the patella edge through the recesses 110, 112, 114, 110C, 112C, 114C, 110D, 112D, 114D and comparing the patella edge with the sizing indicia 116, 116C, 116D. The surgeon would then select an appropriately sized trial portion 20B and assemble the selected trial portion 20B on the base portion 16B, 16C, 16D by inserting the pegs 100, 102, 104 into the drill guide bores 50B, 52B, 54B, 50C, 52C, 54C, 50D, 52D, 54D in the base portion 16B, 16C, 16D. The surgeon would then trial the assembly by moving the patient's knee through flexion and extension. During trialing, the surgeon may rotate or pivot the base portion 16B, 16C on the pedestal 32B, 32C (or the base portion 16D about central longitudinal axis of spike 26D) until the orientation of the trial portion 20B is optimized. The trial portion 20B may then be removed from the base portion 16B, 16C, 16D and holes drilled through the bores 50B, 52B, 54B, 50C, 52C, 54C, 50D, 52D, 54D in the base portion. In these embodiments, the upper surface 106B, 106C, 106D of the base portion 16B, 16C, 16D around the drill guide bores 50B, 52B, 54B, 50C, 52C, 54C, 50D, 52D, 54D would serve to limit the depth of the drilled hole if a drill bit having a depth-setting collar is used. The patella drill guide 10B, 10C, 10D may then be removed from the prepared patella and the patella implant component may be implanted, with its mounting pegs received in the drilled holes and its orientation optimized for proper tracking with respect to the femoral implant component.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected. Other features may be incorporated in the patella drilling system, such as the features disclosed in the following U.S. Provisional patent applications filed concurrently herewith: U.S. Provisional Patent Application Ser. No. 61/540,049 entitled "Clamping Patella Drill Guide", filed by Richard Spencer Jones, Martin W. Roche and Abraham P. Wright; and U.S. Provisional Patent Application Ser. No. 61/540,053 entitled "Patella Drilling System", filed by Raymond E. Randle, Martin W. Roche and Abraham P. Wright. The complete disclosures of these patent applications are incorporated by reference herein.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

We claim:

1. A combination of patella drill guide and trial for use in preparing a resected patellar bone surface to receive a prosthetic patellar implant for a patient's knee joint, the combination of the patella drill guide and trial comprising:
    a body having a flat patella bone-facing surface and a contoured articulation surface spaced above and opposite to the flat patella bone-facing surface;
    at least one spike extending outwardly from the flat patella bone-facing surface in an opposite direction to and away from the contoured articulation surface;
    wherein the contoured articulation surface is linked to the flat patella bone-facing surface and has a curved shape configured for evaluating a track of the patella during flexion of the knee joint;
    wherein:
    the body of the combination of the drill guide and trial has a plurality of drill guide bores extending through the flat patella bone-facing surface, the body and the contoured articulation surface along parallel longitudinal axes;
    each of the drill guide bores has a length extending from the flat patella bone-facing surface to the contoured articulation surface;
    the length of one of the drill guide bores is greater than the length of another one of the drill guide bores;
    the flat patella bone-facing surface has a periphery; and
    the body has a varying thickness between the flat patella bone-facing surface and the contoured articulation surface, the thickness of the body being greatest at a position spaced from the periphery of the flat patella bone-facing surface,
    a line intersecting the greatest thickness of the body and perpendicular to the flat patella bone-facing surface intersects the flat patella bone-facing surface at a position spaced from the periphery of the flat patella bone-facing surface.

2. The combination of the patella drill guide and trial of claim 1, wherein the at least one spike comprises a plurality of spikes.

3. The combination of the patella drill guide and trial of claim 1, wherein each of the drill guide bores has a first larger diameter portion aligned and connected with a second smaller diameter portion, the first larger diameter portion of each of the drill guide bores extending through the contoured articulation surface and the second smaller diameter portion extends from the first larger diameter portion to the flat bone-facing surface.

4. The combination of the patella drill guide and trial of claim 1, wherein the contoured articulation surface has a shape that matches a shape of the prosthetic patellar implant.

5. The combination of the patella drill guide and trial of claim 1, wherein the contoured articulation surface is asymmetric.

6. The combination of the patella drill guide and trial of claim 1, wherein the body comprises a base portion and a trial portion, wherein the base portion defines the flat patella bone-facing surface and the trial portion defines the contoured articulation surface.

7. The combination of the patella drill guide and trial of claim 1, further comprising a rotatable member mounted in a recess in the flat patella bone-facing face, wherein the at least one spike extends outward from the rotatable member and a position of each of the drill guide bores with respect to the resected patellar bone surface changes as the flat patella bone-facing surface is rotated on the at least one spike.

8. The combination of the patella drill guide and trial of claim 7, wherein the at least one spike comprises a plurality of spikes.

9. The combination of the patella drill guide and trial of claim 1, wherein the flat patella bone-facing surface and the contoured articulation surface are integral.

10. The combination of the patella drill guide and trial of claim 1, further comprising a handle extending outward from the flat patella bone-facing surface and a clamping mechanism connected to the handle.

11. The combination of the patella drill guide and trial of claim 1, wherein the plurality of the drill guide bores comprise three drill guide bores spaced in a triangular pattern.

12. The combination of the patella drill guide and trial of claim 11, wherein the at least one spike is positioned between the three drill guide bores.

* * * * *